US012059510B2

(12) United States Patent
Baer

(10) Patent No.: US 12,059,510 B2
(45) Date of Patent: Aug. 13, 2024

(54) BIODEGRADABLE TWO-LAYERED MATRIX FOR PREVENTING POST-SURGICAL ADHESIONS

(71) Applicant: Hans Ulrich Baer, Freienbach (CH)

(72) Inventor: Hans Ulrich Baer, Freienbach (CH)

(73) Assignee: Hans Ulrich Baer, Freienbach (CH)

( * ) Notice: Subject to any disclaimer, the term of this patent is extended or adjusted under 35 U.S.C. 154(b) by 542 days.

(21) Appl. No.: 17/435,501

(22) PCT Filed: Mar. 3, 2020

(86) PCT No.: PCT/EP2020/055510
§ 371 (c)(1),
(2) Date: Sep. 1, 2021

(87) PCT Pub. No.: WO2020/178271
PCT Pub. Date: Sep. 10, 2020

(65) Prior Publication Data
US 2022/0133959 A1    May 5, 2022

(30) Foreign Application Priority Data

Mar. 4, 2019   (EP) ..................... 19160449

(51) Int. Cl.
*A61L 31/06* (2006.01)
*A61L 31/04* (2006.01)
*A61L 31/14* (2006.01)

(52) U.S. Cl.
CPC ............ *A61L 31/06* (2013.01); *A61L 31/044* (2013.01); *A61L 31/146* (2013.01); *A61L 31/148* (2013.01)

(58) Field of Classification Search
CPC ... A61F 2/00; A61F 2/44; A61L 31/00; A61L 27/18; A61L 27/26; A61L 31/06
(Continued)

(56) References Cited

U.S. PATENT DOCUMENTS

| 7,618,646 B2 | 11/2009 | Goerne et al. |
| 10,039,865 B2 | 8/2018 | Sheetrit et al. |

(Continued)

FOREIGN PATENT DOCUMENTS

| CN | 102316823 A | 1/2012 |
| DE | 10353930 A1 | 2/2005 |

(Continued)

OTHER PUBLICATIONS

Liu et al., "Regulation of ERK 1/2 and SMAD2/3 Pathways by Using Multi-Layered Electrospun PCL-Amnion Nanofibrous Membranes for the Prevention of Post-Surgical Tendon Adhesion." International Journal of Nanomedicine 2020:15 927-942. (Year: 2020).*

(Continued)

*Primary Examiner* — Walter E Webb
(74) *Attorney, Agent, or Firm* — The Webb Law Firm

(57) ABSTRACT

A biodegradable matrix for preventing post-surgical adhesions, in particular after soft tissue repair in abdominal surgery within the body of a mammal is disclosed. The matrix includes a top layer made of a first biocompatible polymer material and a bottom layer made of a second biocompatible polymer material. The first polymer material comprises poly(lactic acid) as a main component and the second polymer material comprises as a main component at least one polymer selected from the group consisting of poly(glycolic acid), poly(lactic acid), poly(glycolic acid-lactic acid) and mixtures thereof, wherein the poly(lactic acid)content of the first polymer material is higher than in the second polymer material, and wherein both layers are formed as porous scaffolds with the top layer being hydrophilic, having a water contact angle of less than 75°, and the bottom layer being hydrophobic, having a water contact angle of more than 90°.

31 Claims, 1 Drawing Sheet

(58) Field of Classification Search
USPC .......................................................... 424/448
See application file for complete search history.

(56) References Cited

U.S. PATENT DOCUMENTS

2007/0166343 A1   7/2007   Goerne et al.
2008/0254091 A1  10/2008   Lee et al.

FOREIGN PATENT DOCUMENTS

| EP | 1270018 A1 | 1/2003 |
| EP | 3135309 A1 | 3/2017 |
| WO | 9951163 A1 | 10/1999 |
| WO | 2004108810 A1 | 12/2004 |
| WO | 2007029913 A1 | 3/2007 |

OTHER PUBLICATIONS

Kim et al., "Control of degradation rate and hydrophilicity in electrospun non-woven poly(D.L-Lactide) nanofiber scaffolds for biomedical applications." Biomaterials 24 (2003) 4977-4985. (Year: 2003).*

Law, "Water-surface interactions and definitions for hydrophilicity, hydrophobicity and superhydrophobicity", Pure Applied Chemistry, 2015, vol. 87:8, pp. 759-765.

Liu et al., "Biomimetic Sheath Membrane via Electrospinning for Antiadhesion of Repaired Tendon", Biomacromolecules, 2012, pp. 3611-3619, vol. 13.

Savaris et al.,"Influence of different sterilization processes on the properties of commercial poly(lactic acid)", Materials Science and Engineering C, 2016, pp. 661-667, vol. 69.

Wan et al., "Characterization of surface property of poly(lactide-co-glycolide) after oxygen plasma treatment", Biomaterials, 2004, pp. 4777-4783, vol. 25.

Wang et al., "Cold atmospheric plasma (CAP) surface nanomodified 3D printed polylactic acid (PLA) scaffolds for bone regeneration", Acta Biomaterialia, 2016, pp. 256-265, vol. 46.

* cited by examiner

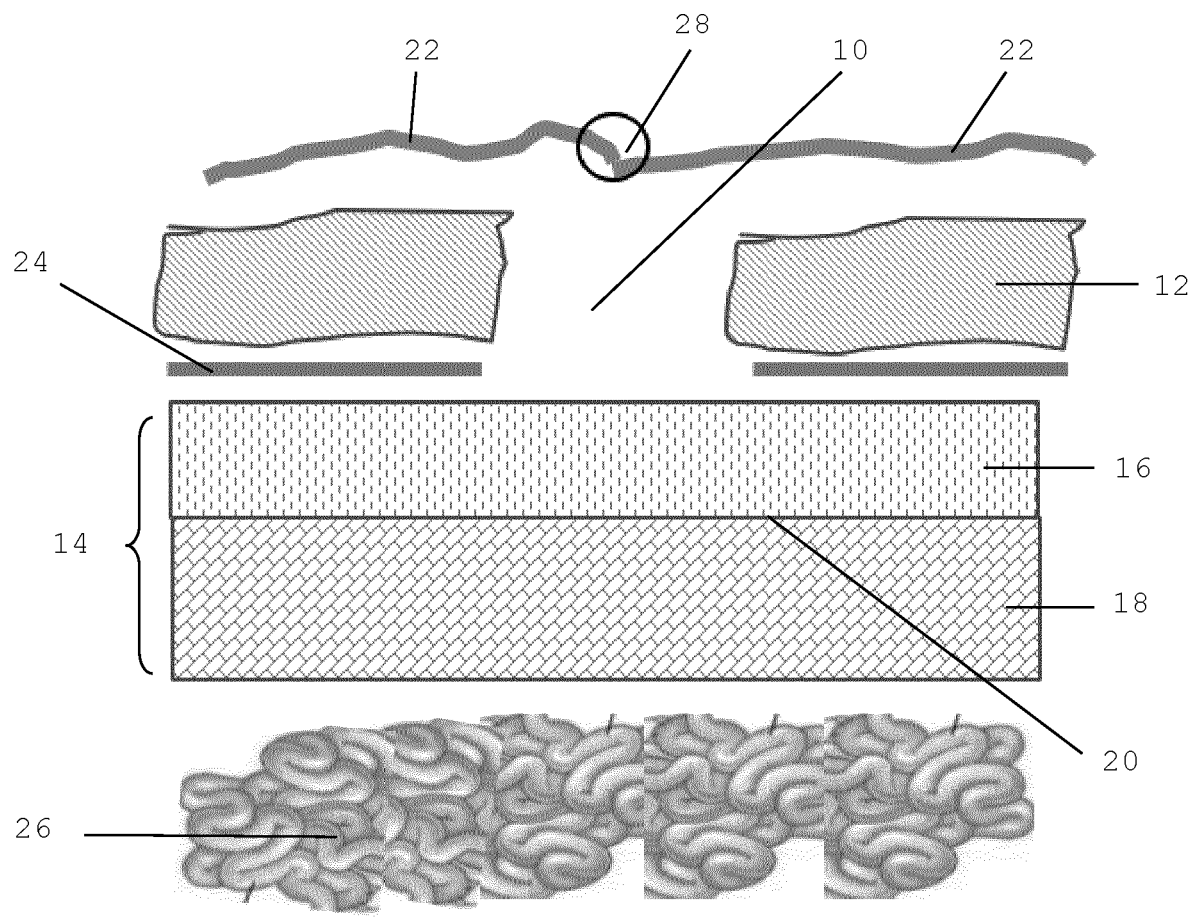

BIODEGRADABLE TWO-LAYERED MATRIX FOR PREVENTING POST-SURGICAL ADHESIONS

CROSS-REFERENCE TO RELATED APPLICATIONS

This application is the U.S. national phase of International Application No. PCT/EP2020/055510 filed Mar. 3, 2020, and claims priority to European Patent Application No. 19160449.5 filed Mar. 4, 2019, the disclosures of each of which are hereby incorporated by reference in their entireties.

BACKGROUND OF THE INVENTION

Field of the Invention

The present invention relates to a biodegradable two-layered matrix for preventing post-surgical adhesions, in particular after soft tissue repair in abdominal surgery, e.g. in hernia repair, within the body of a mammal. Further, the invention relates to a method for preparing the biodegradable matrix.

Description of Related Art

Any trauma to a tissue is usually followed by healing, which is normally accompanied by the formation of collagenous scar tissue. Any physical, chemical or radiation trauma to a biological tissue consisting of various cells, extracellular matrix and connective tissue can result in the death of these cells and structures. The healing process of damaged tissues involves various steps that are also found in inflammatory processes. Specifically, the first steps in wound healing involve removal of necrotic tissues, dead cells and debris. In a second step, the removed tissues are replaced inter alia by inflammatory cells and fibroblasts that are responsible for the production of collagen in its various forms leading to the formation of scarring tissues. This scar formation is desirable to close the soft tissue defect. However, if tissue damage occurs two or more tissues that are in close proximity to each other, the scarring process may also lead to the formation of an undesirable connection of originally separate tissues. This connection is generally referred to as adhesion formation.

In surgical procedures, multiple tissue trauma has usually occurred beforehand and/or is caused by the incision made by the surgeon to reach the surgical site. In consequence, post-surgical adhesions between tissues and/or organs are among the most common complications occurring after any type of surgery. Events such as excessive bleeding and/or inflammation, or intimate contact between tissues substantially increase the probability of adhesion formation at the trauma site. The consequences for the patients caused by such adhesions are often chronic pain and functional disorders, and in many cases will require re-operation.

Adhesions can occur in various forms and strength. In the field of abdominal surgery, adhesion formation is of particular concern. Adhesions in the abdominal area are often the result of an abdominal trauma, which is common in motor vehicle collisions, or they are caused by surgical procedures. As regards the latter cause, it was found that intra-abdominal adhesions often occur at the site of surgical or interventional procedures for which the abdominal wall must be opened through all abdominal layers and the peritoneum. After suturing the incision, the scarring process involves all abdominal layers, in particular also in the area of the peritoneum along the incision. As a result, physiological healing processes within the abdomen are likely to cause adhesion between the tissues of the peritoneum and the adjacent intraabdominal organs. Such adhesions have shown to occur in the form of dense adhesions forming wide bands or as strong, tense strings with a few millimeters of diameter that may traverse the entire abdominal cavity. Extreme forms of abdominal adhesions were even found to cover entire areas of the abdomen, which makes a dissection between e.g. small bowel loops and the peritoneum impossible and often leads to perforation of small or large bowel loops during surgical exploration.

While being undesirable in general, the occurrence of post-surgical adhesions is of particular concern in surgical hernia repair. A hernia is a condition defined as the abnormal displacement of an organ or tissues that protrude through the wall of a cavity. Although hernias can occur in a variety places, most commonly they involve the abdomen, specifically the abdominal wall where the most common site is the groin. Groin hernias are mostly of the inguinal type but may also be femoral. Abdominal hernias occur at specific sites within weak spots in the abdominal wall, such as hiatus, umbilical, periumbilical, or Spiegel hernias, but they may actually occur anywhere in the abdominal wall. A special type is the incisional hernia, which is a hernia that occurs in the area of a past surgical incision or interventional operation.

Traditionally, a hernia would be repaired by an open hernioplasty with sutures. During the months following the hernia operation, the repaired site would gradually gather scar tissue, such that the hernia defect becomes closed and reinforced.

Unfortunately, the process of scar tissue formation has shown to be impaired in some patients, which after hernia repair results in the formation of a further hernia, i.e. a so-called hernial relapse or recurrence. Therefore, in particular for the repair of larger hernias or in case of a hernial relapse, mesh implants are nowadays commonly used for the reconstruction and reinforcement of the abdominal wall. Nowadays, the commercially available meshes used in surgical soft tissue repair are either non-degradable or they are fully degradable and are absorbed within the patient's body after a certain time. The fully degradable meshes (often referred to as "biological" meshes) were developed in the hope that they prevent adhesion formation.

Unfortunately, while helpful to provide additional stability to the repaired area of the former soft tissue defect, both non-degradable and also biodegradable meshes have shown to cause post-surgical adhesions. In particular when so-called "IPOM" meshes, i.e. "intra-abdominal pre-peritoneal on lay meshes", are used to cover defects in the abdominal wall, the formation of undesirable inflammatory or fibrous bands or collagenous scars connecting the mesh and intra-abdominal structures have shown to be the cause of recurrent pain and small or large bowel obstruction. If the latter is not diagnosed in time, it can cause infarction of the bowel, which generally necessitates larger surgical and high-risk procedures. For that reason, in case of abdominal hernia repair, the formation of post-surgical adhesions can be particularly severe to the patient's well-being.

In order to prevent or at least minimize the formation of post-surgical adhesions, attempts were made to isolate the damaged tissue and separating it from any adjacent tissue with a biocompatible material. As a result, adhesion barriers have been developed, which are nowadays available in the form of physical films, fabrics, gels or other materials that are applied between layers of tissues at the end of a surgery before the incision site is closed. While in place, the adhesion barrier acts as a physical barrier to separate traumatized tissue surfaces so that fibrin formation between the healing surfaces is prevented. Examples of commercially available adhesion barriers for use in surgical procedures include for instance:

Preclude® is a thin sheet of porous ePTFE (expanded polytetrafluorethylene; also called GoreTex). It provides a non-sticky, microporous insert, which is biocompatible and non-inflammatory. However, it is non-absorbable and non-degradable, so it requires a subsequent operation to remove it. Also, it must be sutured to tissue in place. For this reason, it was not approved for adhesion prevention in the USA.

Seprafilm® (made by Genzyme) is a clear, sticky film composed of sodium hyaluronic acid with carboxymethyl cellulose (CMC). It sticks to the tissues to which it is applied and is slowly absorbed into the body over a period of seven days. It is approved for use in certain types of pelvic or abdominal surgery.

Interceed® (made by Johnson & Johnson) is a knitted fabric composed of a modified cellulose that swells and eventually gels after being placed on the injured site, and, like Seprafilm, forms a barrier and then is slowly absorbed over a period of days. It is approved for use in pelvic surgery.

However, most of these currently available anti-adhesion barriers do not entirely prevent adhesion formation. They are particularly inadequate for use in hernia repair surgery, because in this case it is not sufficient to prevent the formation of connecting tissues between the healing abdominal wall and the underlying intraabdominal organs but it is at least as important to ensure that there is sufficient tissue growth from adjacent tissues into the area of the hernia, such that the gap in the abdominal wall is securely closed. Particularly if biodegradable (temporary) meshes or scaffolds are used to close a hernia it is essential to induce fibrogenesis and scar formation, i.e. the processes involved in wound healing, to form a stable scar plate that prevents recurrent hernia formation. Therefore, successful hernia repair requires means that induce fibrinogenesis and formation of bridging tissue to close the soft tissue defect, yet without provoking adhesions.

SUMMARY OF THE INVENTION

The problem solved by the present invention is therefore to provide a biodegradable matrix, which allows for rapid, safe and stable closure of a soft tissue defect, in particular a hernia defect, while reducing adhesion formation. At the same time, the matrix shall be easy and inexpensive to manufacture and allow for its use in conventional open and laparoscopic surgical methods.

This problem is solved by the matrix described herein. In line with the present invention, a biodegradable matrix for preventing post-surgical adhesions in surgical soft-tissue repair, in particular following abdominal surgery, within the body of a mammal is provided. More specifically, the inventive matrix is particularly well suited to cover areas of the peritoneum or abdominal wall that were injured during abdominal surgery or due to a hernia.

BRIEF DESCRIPTION OF THE DRAWING

FIG. 1 shows a schematic drawing of a section through a soft tissue defect, specifically a hernia, repaired with the aid of a matrix in accordance with the present invention.

DETAILED DESCRIPTION

The term "matrix", as used throughout this application, refers to a three-dimensional support, e.g. a mesh or a scaffold, with a sponge-like structure, which is suitable for being colonized by cells. Specifically, the matrix of the present invention has a sponge-like structure with interconnected pores of different sizes. In this sense, the matrix serves as a three-dimensional template which can be colonized by cells or tissue. This colonization can take place in vitro or in vivo. Furthermore, the matrix serves, in connection with transplantations, for locating the transplant and also as a place holder for tissue which is gradually formed in vivo.

The expression "biodegradable" refers to a material which can be converted into metabolizable products in living organisms (or body fluids or cell cultures derived from living organisms). Biologically degradable materials include, for example, polymers which are bioresorbable and/or bioerodable. "Bioerodable" denotes the ability to be soluble or suspendable in biological liquids. Bioresorbable means the ability to be able to be taken up by cells, tissues or fluids of a living organism.

In line with the present invention the matrix includes a porous top layer made of a first biocompatible polymer material comprising poly(lactic acid) (generally abbreviated as "PLA") as a main component and optionally at least one further polymer selected from the group of poly(glycolic acid) (generally abbreviated as "PGA"), poly(glycolic acid-lactic acid) generally abbreviated as "PLGA") and mixtures thereof. The term "main component" thereby means that the PLA content of first polymer material is higher than the content of any further polymer that may be present in the first polymer material.

The matrix further includes a porous bottom layer made of a second biocompatible polymer material comprising as a main component at least one polymer selected from the group of poly(lactic acid) [PLA], poly(glycolic acid) [PGA], poly(glycolic acid-lactic acid) [PLGA] and mixtures thereof, wherein the content of poly(lactic acid) in the first polymer material is higher than in the second polymer material. The term "mixtures thereof" thereby also includes co-polymers of the named polymers.

As "biocompatible polymers", the polymers shall be biologically tolerated and not cause rejection when brought into a living organism. For the present invention, biocompatible polymers also encompass polymers which are recognized by a host as being foreign but whose rejection can be suppressed by appropriate immunosuppression.

Both layers of the matrix are formed as porous scaffolds comprising a sponge-like structure with interconnected pores of different sizes. In this regard, the term "porous" refers to a structure comprising pores, i.e. cavities or void regions. These pores may have a round shape and/or an angular shape in a 2-dimensional section and/or a canted shape when seen 3-dimensionally. The shape of the pores may also be characterized by extensions such that it can be compared with the shape of nerve cells. Although in general, the term "pores" also refers to cavities formed by filaments enclosing a void region, pores within the meaning of the present invention are cavities formed in a sponge-like structure. The cavities are thereby enclosed by walls, as in natural sponges or corals. At least some of the pores or cavities are interconnected, meaning that the pore walls between two adjacent pores can comprise holes, forming a connection between said adjacent pores. This is in contrast to a knitted net structure. At least some of the pores are thereby interconnected, such that they divide the space into a fluidically connected interstitial network. This way, cells can spread through the matrix structure. In this regard, it is to be noted that the pores formed within the top layer and those within the bottom layer may be structurally distinct from one another, e.g. with regard to their shape, size and/or interconnectivity.

One key element of the present invention is that both layers are biodegradable and are in the form of porous scaffolds, whereby the top layer is hydrophilic, having a water contact angle of less than 75°, preferably less than 60°, and the bottom layer is hydrophobic, having a water contact angle of more than 90°.

The term "contact angle" as used in the context of the present application relates to the contact angle of water on a surface, i.e. to the angle formed at the interface where water meets the surface. Thereby, "water" used for the contact angle measurement relates to pure water, specifically ultrapure water. In particular, the contact angle measurement is carried out by the sessile drop method (e.g. by means of a device of the type EasyDrop DSA20E, Krüss GmbH) using a drop size of 0.3 or 0.1 µl. Contact angles are generally calculated by fitting a circular segment function to the contour of the droplet placed on the surface ("Circle Fitting" method). The term "hydrophilic" or "hydrophilicity" as used in the context of the present invention refers to a water contact angle of a surface area on the matrix being below 75°.

On the other hand, the term "hydrophobic" or hydrophobicity shall be understood as a substrate having a surface area with a water contact angle above 90°. With respect to the hydrophobic bottom layer of the inventive matrix, it has preferably a water contact angle above 120°. Hydrophobic properties are generally a problem with synthetic polymers, such as PLA; PGA and PLGA, and are often increased by many post-processing methods, such as UV-treatment.

Notably, the top layer of the inventive matrix is hydrophilic despite comprising the above-mentioned generally hydrophobic biodegradable synthetic polymers. Hydrophilic properties are important for promoting cell penetration and adhesion.

It was discovered that thanks to the first polymer material comprising PLA as a main component, the hydrophilic properties of the top layer can be enhanced by certain post-processing methods, in particular a low temperature and low pressure plasma treatment step—which will be described in detail further below. The term "plasma" thereby generally refers to an excited and radicalized gas, i.e. an electrical conducting process gas involving electrons and ions. Plasma is commonly generated by means of electrodes in a vacuum chamber (so-called "RF plasma approach"), but it can also be generated using capacitive or inductive methods, or microwave radiation. More details in this respect are given in the experimental section further below.

The inventive matrix provides multiple beneficial effects: On the one side it has been found that the hydrophilic properties of the matrix' top layer promote tissue ingrowth of e.g. peritoneal cells, smooth muscle cells and fibroblasts from adjacent tissue into the wound that is to be closed, e.g. a hernia, and enables even cell distribution on and throughout top layer. In addition, the porous nature of the top layer provides a growth-stimulating environment for the cells that help constructing extracellular matrix tissue and various types of collagen fibres, thereby forming a scar plate closing the tissue defect. First, the growing scar plate will establish a firm connection between the degradable (and thus temporary) matrix and the rims of the tissue defect. In case of a hernia, the scar plate will form throughout the matrix to close the gap within the abdominal wall. Over time, while the degradation of the matrix continues, the newly formed scar tissue will gradually take over the necessary support function by creating additional cicatrisation, thereby preventing re-opening of the wound or recurrent hernia formation.

On the other side it was found that the hydrophobic properties of the matrix' bottom layer effectively hinders attachment of most cell types, in particular inflammatory proteins, or hydrophilic fluids to the bottom surface of the matrix—which prevents unwanted tissue adhesion formation. Specifically, when tested in abdominal hernia repair, the hydrophobic properties of the bottom layer of the inventive matrix successfully prevented infiltration of peritoneal or other bodily fluid into the matrix and minimized undesired tissue adhesion formation between the hernia repair and the intra-abdominal structures, in particular the small bowel.

In summary, the matrix of the present invention provides a temporary closure of the soft tissue defect—for instance an abdominal hernia—and has the following benefits:

On the one hand, the porous hydrophilic top layer facing the hernia promotes ingrowth and proliferation of cells, such as muscle cells and fibroblasts, that will form new scar tissue taking over the continuously decreasing support function of the matrix. In the end, after complete degradation of the matrix (i.e. when the polymeric components of the matrix have been absorbed), no permanent foreign material will be left within the patient's body.

On the other hand, the hydrophobic properties of the matrix' bottom layer prevents the attachment of inflammatory cells fibrin or debris, to the matrix from the intraperitoneal side (i.e. the side of the matrix facing away from the hernia and towards the abdominal cavity), such that the occurrence of inflammation and the formation of adhesive tissue growth between the matrix or the newly-formed scar plate and the underlying abdominal tissues is avoided.

Although particularly useful in hernia repair, the inventive matrix can be used to aid the healing process after surgical intervention in general. For instance, if abdominal surgery is performed and intraabdominal inflammation is present, it is important to provide a barrier between the inflamed intraabdominal tissue and overlying tissues that have been cut to access the surgical site—irrespective of the wound size, e.g. even if only a small incision is made in a minimally invasive approach. The hydrophobic layer can therefore provide such a barrier and the hydrophilic layer can promote the healing process of the surgical wounds.

Another advantage of the inventive matrix is that both layers are porous, which provides the option to have pharmacologically active agents—such as epidermal growth factor, platelet derived growth factor, transforming growth factor beta, angiogenesis factor, antibiotics, antifungals, spermicidals, hormones, enzymes, and/or enzyme inhibitors—incorporated into the layers, preferably the top layer, to deliver these agents to the wound site and positively affect cell growth, such as collagen types IV and V, fibronectin, laminin, hyaluronic acid and proteoglycans, in and adjacent to the top layer area.

To facilitate cell attachment and growth throughout the top layer it is preferred that the entire scaffold structure of the top layer has a hydrophilic surface, i.e. a surface having a water contact angle of less than 75°. Such hydrophilic properties have been achieved by subjecting the matrix to plasma treatment at a temperature below 50° C. and preferably at low pressure within the range of in the range of $10^{-2}$ to $10^{-6}$ bar, preferably within the range of 0.1 to 1.0 mbar.

Since increasing hydrophilicity has shown to correlate with improved cell attachment and proliferation, the top layer of the matrix has preferably a water contact angle of less than 60°, more preferably less than 45° and even more preferably less than 25°. Most preferably, the water contact angle of the hydrophilic surface on the top layer of the matrix is within the range of 0° to 10°, which means that the top layer is "super-hydrophilic".

The top and the bottom layer may be provided as a one entity structure, i.e. wherein the two layers are integrally formed or firmly connected to one another on multiple locations. Alternatively, the two layers may also be provided as two individual structures that are separate from one another. One example would be that the top layer and bottom layer are both provided in a sheet-like shape and are simply loosely stacked on top of each other.

In a particularly preferred embodiment, the material compositions of the two layers differ from one another. The difference may be either with respect to the polymer type and/or content of a specific polymer in the polymer material. For instance, both layers may consist of the same type of polymers, yet with different polymer ratios. Alternatively, the top layer and the bottom layer may differ with respect to the type of polymers present in the polymer material.

In one preferred embodiment the first polymer material of the top layer consists to at least 70% of PL). (Notably, the term "PLA" encompasses all chiral forms of PLA, i.e. PLLA, PDLA and mixtures (co-polymers) thereof.) This means that the top layer may be formed entirely of PLA or it may consist of 70% or more PLA and 30% or less of at least one additional different polymer, e.g. PLG. If at least one additional polymer is present, the PLA and the other polymer(s) can form a co-polymer or the top layer can be provided as two separate components—e.g. a PLA basic structure with a coating of the other polymer(s). PLA was found to have good tensile strength and high modulus. In addition, PLA was found to be beneficial with respect to achieving and maintaining hydrophilic properties. More specifically, it was found that for porous structures made of a material with a high PLA-content, e.g. if the first polymer consists of at least 70% PLA, hydrophilicity of the surface could not only be significantly enhanced by a plasma treatment as described herein—but the hydrophilicity could also be maintained over a prolonged time. In fact, the hydrophilicity could also be maintained after sterilizing the matrix with hydrogen peroxide (as will also be described further below). Thanks to the hydrophilic properties, the top layer facilitates cell attachment to and ingrowth into the matrix.

Pure PLA has, however, the drawback of being less stable, i.e. less strain-resistant, than e.g. PGA. Nevertheless, since the bottom layer may be used to provide additional stability to the matrix, the top layer may also essentially consist of PLA. A specific example of a preferred PLA material is poly(L-lactide) that is commercially available from Sigma Corporation (PLLA catalogue number P1566) with a molecular weight of 85,000-160,000 Da. A suitable alternative is PLLA from Durect Corporation (Lactel® catalogue number B6002-2).

As mentioned, the polymer material of the top layer may be based on PLA, yet combined with one or more other polymer(s) to increase the top layer's more stability. One preferred additional polymer is PGA. Co-polymers of PLA and PGA—so-called "poly-lactide-co-glycolic acid" (abbreviated as PLGA or PLG) can be purchased in different PLA/PGA ratios with well-defined physical properties. By varying the copolymer ratio of PLA to PGA, the different copolymers of PLGA offer a large spectrum of flexibilities and variable degradation rates from a few days to years.

In a preferred embodiment, the second polymer material of the bottom layer of the matrix preferably consists of poly(glycolic acid-lactic acid) [PLGA]. In general, the higher the proportion of PGA in the PLGA composition, the higher the stability of the polymer. Also, the higher the PGA content in the second polymer material, the higher is the hydrophobicity of the bottom layer, even after a plasma treatment that is used to increase the hydrophilicity of the top layer. Again, the bottom layer will generally provide additional stability to the matrix, whereas the top layer provides a hydrophilic, cell-friendly environment that increases the survival and proliferation rate of cells on and within the top layer. As such, the second polymer material of the bottom layer will generally have a higher PGA content than the first polymer material of the top layer (since the first polymer material of the top layer has a higher PLA content than the second polymer material of the bottom layer).

In one embodiment, both layers consist of PLGA, yet with different ratios of PLA to PGA. A preferred polymer material for the top layer is a 85:15 mixture of poly(L-lactic acid) (PLLA) and PGA—i.e. a polymer mixture having a lactic acid (PLA) content of about 85 mol % and a glycolic acid (PGA) content of about 15 mol %. Such a 85:15 mixture can be purchased, for instance, from Evonik Industries AG (Essen, Germany) or from Durect company (Cupertino, CA, USA) under the brand name RESOMER® RG 858 or LACTEL® Absorbable Polymers. The bottom layer poly(D, L-lactide-co-glycolide) may be a 50:50 mixture of PLLA and PLG, e.g. RESOMER® RG 502. Further preferred polymer mixtures for the top and/or bottom layer are poly (D,L-lactide-co-glycolide) 65:35, e.g. RES OMER® RG 653; poly(D,L-lactide-co-glycolide) 75:25, e.g. RESOMER® RG 752; poly(D,L-lactide-co-glycolide) (always chosen such that the PLA content of the first polymer material is higher than the PLA content of the second polymer material).

Preparation methods for preparing porous meshes from the above-mentioned synthetic polymers are well known in the art. One possibility is the use of a salt-leaching technique, as described for instance in EP 2256155.

It is preferred that the top layer comprises or is at least partially covered with at least one natural polymer selected from the group consisting of collagen, gelatin, laminin, fibrinogen, albumin, chitin, chitosan, agarose, hyaluronic acidalginate and mixtures thereof, whereby collagen is preferred. The natural polymer provides the top layer with additional stability, hydrophilicity and facilitates cell proliferation. Preferably, the porous scaffold of the top layer is coated or covered with the natural polymer, such that the underlying porous structure of the top layer is not changed by the coating. More specifically it is preferred that the natural polymer covers the surface of the sponge-like structure without forming additional three-dimensional structures within the pores of the sponge-like structure of the top layer. This ensures that the coating does not negatively the affect the cells' ability to penetrate and spread within the top layer of the matrix.

In a particularly preferred embodiment, the second polymer material of the bottom layer essentially consists of PLGA or PGA and the first polymer material of the top layer of the matrix essentially consists of PLA alone (which may be covered with a natural polymer selected from the ones mentioned in the previous paragraph). Of the mentioned natural polymers, collagen is most preferred. This is because collagen is a biomolecule of the extracellular matrix (ECM) and the major component of skin and bone. Thanks to its nano-fibrous architecture it is particularly effective in promoting cell adhesion, growth and differentiated function in tissue cultures. However, it has also been found that the presence of collagen in the first polymer material particularly enhances the hydrophilic properties of the top layer of the matrix.

Notably, the term "collagen" as used in the context of the present invention encompasses naturally derived collagens and synthetically produced collagens as well as collagen derived substances, such as gelatine, which is a hydrolysed form of collagen. Also, the term "collagen" further includes all types of collagen. For instance, the natural polymer may include only one specific type of collagen, e.g. type I, or may consist of a mixture of collagen types, e.g. a mixture of type I collagen and type IV collagen. In the latter case, preference is given to the mixture containing the proteins in approximately equal percentages by weight. Collagen type I is most preferred, since it is one of the main components of natural blood vessels and provides the secondary structure with cellular attachment sites as well as tensile strength. In addition, it is one of the main components of natural blood vessels and provides a natural attachment site for cells involved in the wound healing process. Last but not least, the degradation product of collagen type I to III have also been shown to induce a chemotactic attraction of human fibroblasts, which is particularly beneficial for the intended use of the inventive matrix in surgical soft tissue repair. In a preferred embodiment, at least one of the top layer and the bottom layer, preferably both layers, has/have a flat sheet-like shape and is/are elastically deformable to allow folding or rolling thereof. In particular, it is preferred that the whole matrix is elastically deformable, such it can be folded or rolled, and it can return to its original shape. This allows insertion of the matrix through a trocar in a laparoscopic procedure, e.g. allowing an IPOM insertion of the matrix.

In general, each layer has preferably a thickness within the range of at least 0.1 mm to 20 mm, more preferably from about 1 mm to about 10 mm, even more preferably from about 1 mm to about 3 mm. It goes without saying that the two layers can also have different thicknesses.

If provided in sheet-like shape, the outer shape (when seen in top view or in longitudinal section) of the matrix can be of any kind, for example rectangular, square, circular, oval, etc., and can also be cut to suit the shape of the soft-tissue defect that is to be repaired. Preferably, the outer shape of the cross-section is circular or oval to avoid any sharp edges.

It is further preferred that the top and bottom layer—and preferably the entire matrix—has a porosity of at least 80%, preferably at least 85%, more preferably at least 90%. This porosity ensures that nutrients can diffuse through the matrix to provide a cell-friendly environment in the hydrophilic top layer that promotes cell proliferation and development. In addition, the porous structure allows incorporation of growth factors or other cell-growth stimulating molecules into the matrix, in particular the top layer.

As regards the degradation time of the matrix within the body—which will usually occur through bio-absorption of its components—it is preferred that the top layer has a faster degradation rate than the bottom layer. In particular, the degradation time of the top layer in the body preferably goes hand in hand with the formation of scar tissue that safely closes the soft tissue defect when the matrix has degraded. In particular in hernia repair it is highly preferred that the bottom layer still provides additional support by the time that the top layer has fully degraded, as this prevents the former hernia from re-opening until the scar plate that is formed over and within the degrading top layer is strong enough to withstand the abdominal pressure. In addition, the hydrophobicity of the bottom layer helps to establish a physical barrier between the scar tissue that is in formation and the underlying abdominal organs. Therefore, during the first few months when that cell growth is most prominent, adhesion formation between the new scar tissue and the intraabdominal organs is effectively prevented by the hydrophobic properties of the bottom layer. By the time that the formation of a stable scar plate that covers the former hernia is completed, the bottom layer will continue to degrade, such that generally after 12 to 24 months after implantation of the matrix, no foreign material will be left within the body.

In a preferred embodiment, the matrix has a total degradation time in a living organism of less than 24 months, with the top layer having a preferred degradation time of less than 6 months, preferably less than 4 months, and the bottom layer having a preferred degradation time of at least 4 months, preferably between 4 and 24 months. As such, the bottom layer will provide an additional support function during the first 4 to 12 months. After 24 months, the bottom layer will generally be more or less fully degraded as well.

In a specific embodiment it is preferred that the degradation time for the top layer in the living organism is between 1 and 4 months, preferably about 3 months. For the bottom layer, on the other hand, it is preferred that the degradation time in the living organism is between 6 and 12 months.

Another advantage of the inventive matrix is that it allows incorporation of agents into the matrix, in particular the top layer, that are subsequently delivered to the soft tissue defect. Preferred agents are collagen types IV and V, fibronectin, laminin, hyaluronic acid, and proteoglycans. Similarly, pharmacologically active agents such as growth factors, antibiotics, antifungals, spermicidals, hormones, enzymes, and/or enzyme inhibitors can also be incorporated into the matrix.

To promote scar tissue formation in and around the area of the top layer it is preferred that the top layer further includes growth factors. Growth factors typically act as signalling molecules between cells and often promote cell differentiation and maturation. For example, epidermal growth factor (EGF) enhances osteogenic differentiation, while fibroblast growth factors (FGF) and vascular endothelial growth factors (VEGF) stimulate blood vessel differentiation (angiogenesis). In view of the matrix' use in soft tissue repair, the top layer preferably includes at least one growth factor selected from the group consisting of interleukins, acidic fibroblast growth factor, basic fibroblast growth factor (b-FGF), epidermal growth factor, insulin like growth factor, insulin like growth factor binding protein, platelet-derived growth factor (PDGF), transforming growth factor alpha, transforming growth factor beta, VEGF, and hepatocyte growth factor (HGF). These growth factors are important for regulating cell proliferation and differentiation, protein synthesis and ECM (extracellular matrix) remodelling. In particular, b-FGF, PDGF, VEGF, and HGF have shown to increase granulation, epithelialisation and capillary formation through angiogenic cytokines secretion. They have also proven to inhibit neutrophil and macrophage migration to wound location by secreting factors that inhibit migration and both TL-1α and IL-1β suppression, and to secrete anti-inflammatory factors which prevent apoptosis and improve wound healing.

In a particularly preferred embodiment, the top layer includes growth factors that are added to the matrix, in particular the top layer, in the form of secretome derived from placental mesenchymal cells. The commercially available secretome derived from (or at least comprising) stem cells from human Wharton's Jelly Stem Cell (CM-hWJSC) that were cultured in hypoxia condition was found to be particularly effective in stimulating cell attachment to and cell ingrowth into the top layer of the matrix. This stem cell secretome can be purchased e.g. from Stem Cell and Cancer Institute (PT. Kalbe Farma Tbk.).

For the preparation of the matrix, a method including the following steps can be used:
 a) preparing a first mixture I consisting of salt particulates and a dissolved first polymer material comprising poly(lactic acid) [PLA] as a main component and optionally at least one further polymer selected from the group consisting of poly(glycolic acid) [PGA], poly(glycolic acid-lactic acid) [PLGA] and mixtures thereof;
 b) spreading the first mixture I on a surface to form a first layer;
 c) preparing a second mixture II consisting of salt particulates and a dissolved second polymer material comprising as a main component at least one polymer selected from the group consisting of PGA, PLA, PLGA and mixtures thereof, wherein the content of PLA in the first polymer material is higher than in the second polymer material;
 d) depositing a layer of the second mixture II of step c) on top of the first layer;
 e) drying the resulting structure to obtain a two-layered biodegradable matrix with a top layer of the first polymer material and a bottom layer of the second polymer material; and
 f) plasma treatment of the matrix with an oxidized gas plasma at a temperature below 50° C.

The plasma treatment was found to increase the hydrophilic properties of the surface of the top layer, without having detrimental effects on the stability or structural integrity of the matrix. Plasma treatment of PGA structures, on the other hand, was found not to enhance the hydrophilicity. Due to the higher PLA content in the top layer compared to the bottom layer, the plasma treatment was particularly effective for enhancing and also maintaining the hydrophilic properties of the top layer, yet not or only to a small degree of the bottom layer.

The ionized gas plasma used for the plasma treatment is preferably selected from the group consisting of helium, argon, nitrogen, neon, silane, hydrogen, oxygen and mixtures thereof. Preferred treatment gases are hydrogen, oxygen and nitrogen, in particular oxygen.

More specifically, the plasma treatment preferably involves a low temperature, low-pressure plasma treatment, in which the carrier mesh is exposed to an ionized gas plasma at i) a temperature below 50° C., preferably below 40° C., ii) for at least 2 minutes, more preferably 5 to 20 minutes, and iii) at a pressure in the range of $10^{-2}$ to $10^{-6}$ bar, preferably at a pressure within the range of 0.1 to 1.0 mbar.

The term "plasma" thereby generally refers to an excited and radicalized gas, i.e. an electrical conducting process gas involving electrons and ions. Plasma is commonly generated by means of electrodes in a vacuum chamber (so-called "RF plasma approach"), but it can also be generated using capacitive or inductive methods, or microwave radiation.

Instead of the above steps a) to e), the matrix of the present invention may also be manufactured using 3D-printing, electro-spinning and other methods known in the art for the preparation of polymeric scaffolds.

The method may further include a step in which the porous scaffold of the top layer formed of the first polymer material is covered with a natural polymer selected from the group of collagen, gelatin, laminin, fibrinogen, albumin, chitin, chitosan, agarose, hyaluronic acidalginate and mixtures thereof, preferably collagen. This step—if present—is preferably performed before the plasma treatment step f).

In view of its later use as an implant, the matrix of the present invention is then (i.e. after step f)) preferably sterilized. To this end, use is preferably made of a special sterilization technique that has been developed for this purpose. This sterilization technique allows sterilization of heat and/or UV sensitive tissues, in particular polymeric scaffolds, and is therefore not limited to the special matrix described above, but is applicable for all kinds of (heat-sensitive) articles that need to be sterilized.

Nowadays there is no doubt that sterilization is essential for almost any device and article that is used in the medical field, such as instruments, all kinds of implants and any surgical auxiliaries. In theory, numerous sterilization techniques are available, yet they are not all applicable to all substrates. Metal substrates, such as a metal instrument or an implant, for instance, can be subjected to heat sterilization using steam. This technique is typically performed in a steam sterilizer (also referred to as autoclave) using steam typically having a temperature above 120° C. under pressure. Heat sterilization is, however, not suitable if the article to be sterilized is heat-sensitive. In addition, the use of steam is unsuitable for components that are biodegradable and therefore to a certain degree soluble in water. Therefore, biodegradable polymeric substrates that comprise a heat-sensitive natural polymer, such as collagen for instance, cannot be sterilized by hot steam without impairing the molecular structure of the substrate.

As an alternative, a substrate can be subjected to ethylene oxide gas sterilization or plasma sterilization. However, in as far as ethylene oxide is used, the technique has the further drawback of requiring relatively strict safety measures due to the high toxicity of the sterilizing agent.

Further sterilization techniques include radiation sterilization, in particular gamma-sterilization or X-ray sterilization. These techniques, on the other hand, have the major drawback that hydrophilic surface characteristics of the substrate (here the top layer) are usually lost or at least substantially impaired due to the sterilization treatment.

Thus, for sterilizing a two-layered matrix in accordance with the present invention described above, it requires a method that avoids use of heat, i.e. temperatures above 50° C., to preserve the three-dimensional polymeric structure of the matrix. In addition, the method must allow for preservation of the high hydrophilicity of the top layer during and after the sterilization procedure.

In consideration of the above, it has also been an additional object of the present invention to provide a simple process that allows thorough sterilization of the matrix without compromising the hydrophilicity of the top layer.

It has been found that the following procedure meets all these requirements and is therefore particularly well suited for the sterilization of sensitive substrates, such as the two-layered matrix of the present invention. The procedure involves the steps of
 I. providing a two-layered matrix as described in the present application, and II. subjecting the matrix to a hydrogen peroxide containing environment at a temperature below 50° C., preferably below 40° C.; at a reduced pressure within the range of $10^{-6}$ to $10^{-2}$ bar; and for at least 2 minutes.

The surprising finding that this low-temperature hydrogen peroxide sterilization achieves a sterile and hydrophilic biodegradable article opens the possibility of a simple process for sterilizing sensitive materials without negatively affecting their structural integrity and hydrophilic properties. As an additional benefit, the new sterilization method is very simple and straightforward in that no laborious preparation steps are required.

The hydrogen peroxide containing environment can either be provided by $H_2O_2$ plasma treatment or by placing the substrate to be sterilized into a vacuum chamber, together with a source of (generally liquid) hydrogen peroxide. The plasma treatment preferably involves a low-pressure plasma treatment, in which the matrix is exposed to an ionized gas plasma at a pressure in the range of $10^{-2}$ to $10^{-6}$ bar, preferably within the range of 0.1 to 20.0 mbar, and a temperature below 50° C., preferably below 40° C., for at least 2 minutes. Alternatively, the matrix may be placed inside a vacuum chamber and upon applying a pressure that is sufficiently low to evaporate the hydrogen peroxide, the hydrogen peroxide evaporates, and a hydrogen peroxide-containing atmosphere will be created. Particularly preferred (negative) pressures are within the range of 0.1 to 20.0 mbar, such as 6 to 12 mbar.

The sterilization time depends highly on the pressure within the chamber, the treatment temperature and the concentration of the $H_2O_2$ solution. Preferably, the $H_2O_2$ solution comprises $H_2O_2$ in an amount of about 30% by volume or less. Preferred treatment times are at least a few minutes, e.g. 2 to 30 minutes, alternatively at least one hour. If "higher" pressures, in particular above or around 10 mbar, and/or low temperatures, e.g. below 40° C., are applied, or if the $H_2O_2$ concentration is lower than 30%, e.g. 20-25%, treatment times of several hours, e.g. between 10 and 12 hours, are preferred.

As initially mentioned, the two-layered matrix of the present invention is particularly useful for preventing intraabdominal adhesions, e.g. in the field of hernia repair and for preventing recurrent hernias. The present invention therefore also relates to the use of the inventive two-layered matrix in surgical soft-tissue repair, in particular in abdominal surgery, e.g. in hernia repair. Specifically when used for hernia repair the inventive method includes the steps of i. providing a biodegradable matrix having a hydrophilic top layer and a hydrophobic bottom layer as described in the above sections;
ii. making an incision through a patient's skin and abdominal tissues to access a hernia in the abdominal wall;
iii. placing the matrix either above the defect, e.g. the abdominal wall or alternatively beneath the muscle layer of the abdominal wall (sub-lay technique) or as an intraperitoneal on lay mesh (IPOM) below the peritoneum;
iv. closing the incision.

If desired, the matrix may be additionally attached to the abdominal muscles to prevent migration.

Preferred embodiments with respect to the structure of the matrix and its placement within the body of a patient in hernia repair are further illustrated by way of FIG. 1.

The schematic drawing of FIG. 1 shows a defect (gap) 10 in muscle tissue 12 that has been bridged with a matrix 14 of the present invention. Specifically, a biodegradable matrix of the present invention having a porous hydrophilic top layer 16 and a porous hydrophobic bottom layer 18 is provided. The hydrophilic top layer 16 consists of poly (lactic acid) [PLA] and optionally collagen. It has a water contact angle below 10° and is thus super-hydrophilic. The bottom layer 18 of the matrix consists of poly(glycolic acid-lactic acid) [PLGA], e.g. Resomer® RG 503 H from Sigma Aldrich with a lactide: glycolide content of 50:50, and has a water contact angle above 90°. It is thus hydrophobic. The two layers are connected to each other along a common interface 20 and form a single, two-layered matrix unit 14. The hydrophilic properties of the top layer are obtained by plasma treatment of the matrix with an oxygen gas plasma at a temperature below 40° C. and a pressure within the range of 0.1 to 1.0 mbar. This plasma treatment showed to provide the top layer having a high PLA content with hydrophilic properties, whereas the hydrophobic properties of the PLGA bottom layer are essentially not altered by the plasma treatment.

In surgical hernia repair, an incision is made through a patient's skin 22 and abdominal tissues 12 to access a hernia 10 in the abdominal wall. Then, the matrix 14 is placed either above the defect, e.g. the abdominal wall (inguinal hernia repair according to Lichtenstein) or alternatively beneath the muscle layer of the abdominal wall (sub-lay technique) or—as in the case shown in FIG. 1—as an IPOM (intraperitoneal on lay mesh) below the peritoneum 24. The bottom layer 18 will face the intraabdominal organs, in particular the small bowel 26 and the top layer will face the hernia 10. If desired, the matrix 14 may be additionally attached to the abdominal muscles 12 and/or the peritoneum 24 to prevent migration. (Before placing the matrix, the defect in the abdominal wall may also be closed by stitches. The matrix will then be placed above or below the repaired defect to stabilize the suture and help the healing process.) The incision is then closed by closing the overlaying skin 22 by stitches 28.

After implantation, the following processes will generally occur:

As degradable structure, the matrix provides a temporary support structure for cells to migrate into the matrix, in particular the top layer of the matrix, from adjacent tissues and to proliferate. The hydrophilic properties of the top layer facing the hernia promotes ingrowth and proliferation of cells, such as muscle cells and fibroblasts, that will form new scar tissue taking over the continuously decreasing support function of the matrix. The hydrophobic properties of the bottom layer, on the other hand, does the opposite: it prevents the attachment of cells, such as inter alia inflammatory cells, fibrin or debris, to the matrix from the intraperitoneal side, i.e. the side of the matrix facing away from the hernia and towards the abdominal cavity, such that the occurrence of inflammation and the formation of adhesive tissue growth between the matrix or the newly-formed scar plate and the underlying abdominal tissues is avoided.

The top layer has a faster degradation rate than the bottom layer. The degradation of the top layer takes about 3 to 6 months and goes hand in hand with the formation of scar tissue that safely connects the rims of the former hernia with the abdominal wall. By the time that the top layer has fully degraded, the bottom layer still continues to provide additional support against the abdominal pressure and also provides a physical barrier between the newly formed scar tissue and the underlying abdominal organs. Therefore, at the time that cell growth is most prominent, adhesion formation between the scar tissue and the intraabdominal organs is effectively prevented by the hydrophobic properties of the bottom layer. In addition, if intraabdominal inflammation is present, said physical barrier also separates the inflamed tissues from the surgical wound. After about 12 months, when the formation of a stable scar plate covering the former hernia is completed, the bottom layer will generally also be essentially fully degraded and no foreign material is left within the body.

The matrix may be simply placed over the defect or additionally secured in place by stitches or other measures to prevent displacement of the matrix.

Over the days and weeks after insertion of the matrix, cells from adjacent tissues, in particular smooth muscle cells and fibroblasts, will continue to proliferate and build up scar tissue that firmly closes the hernia. Said scar tissue will safely close the hernia at the time that both layers of the matrix have fully degraded.

To prove the above-described effects, the inventive matrix has been tested in vivo by being implanted into rats. Specifically, an experimental abdominal wall hernia in a rat was repaired with the aid of a two-layered matrix in accordance with the present invention. In this experiment, the matrix was placed below the peritoneum as shown in FIG. 1. To keep the implanted matrix in place, the matrix was attached to the muscle tissue by few stitches before closing the skin by stitches. After a healing time of six weeks, the implantation site was re-opened. It was found that no adhesions had formed between the matrix and the underlying small bowel. On the other hand, in an area that was not covered by the matrix, formation of an adhesion band from the liver rim to the abdominal wall was observed. Therefore, the in vivo experiment confirmed that the inventive matrix successfully prevents the formation of post-surgical adhesions.

In the following sections, specific examples of ways to prepare the inventive matrix will be described in detail.

Experimental Data

Preparation of the Matrix

Sodium chloride (NaCl) particulates were ground using mortar and pestle before being sieved to obtain NaCl particulates ranging from 355 to 425 μm. 9 g NaCl particulates were put in a centrifuge tube and dried in a desiccator. The NaCl particulates were then put into an aluminium pan and a PLLA solution prepared of 1 g of PLLA pellets (lactide 100 from Durect Lactel®) in 5 ml of chloroform was poured onto the NaCl particulates. The PLLA solution was mixed with the NaCl particulates and the mixture was then spread evenly in the aluminium pan to form a flat PLLA layer.

Optional Collagen Post-Processing

Some matrices were also provided with a collagen coating on the PLLA layer (which will later form the top layer). To this end, the prepared PLLA layer was dried and detached from the aluminum pan. Then, a collagen solution (Collagen Type I Solution; Wako) was poured in a petri dish. The concentration of the collagen solution was chosen within the range from 0.1 to 5.0 (w/v) %, preferably 1% (w/v). The PLLA layer was immersed in the collagen solution before being placed in another petri dish and frozen in a deep freezer at −80° C. for several hours before freeze-drying (also known as lyophilisation) under a vacuum of <5 mbar (at a temperature between −50° C. and −80° C.) for at least 24 h.

To form the hydrophobic PLGA layer (which will later form the bottom layer), 9.0 g of NaCl particulates were put into a second aluminium pan and a PLGA solution of 1 g of PLGA pellets (lactide 25; glycolide 75. from Durect Lactel®) in 5 ml of chloroform was prepared. The PLGA solution was mixed with the NaCl particulates. Then the PLGA/NaCl-mixture was poured on top of the PLLA layer (either with or without collagen coating) provided in the first aluminium pan and spread evenly to form a matrix with a PLGA layer on top of the PLLA layer.

The PLLA/PLGA-NaCl matrix was detached from the aluminum pan and dried in a vacuum chamber under −0.1 MPa for 3-4 days.

The resulting dried PLLA/PLGA-NaCl matrices were put in a beaker, immersed in ddH$_2$O (twice deionized water) and kept in a linear shaking bath at 25° C. (room temperature), at 60 rpm for 48 hours to leach/wash out the NaCl particulates. The water in the beaker was exchanged every 1-2 hours. The two-layered PLLA/PLGA matrices were removed from the beaker and dried in the fume hood overnight.

The matrices were prepared with pores having a diameter within the range of 355-425 micrometers.

It was found that the PLGA layer can also be prepared first and the PLLA layer in a second step.

O$_2$ Plasma Treatment

The matrices—either with the top layer being coated with collagen or not—were further subjected to a plasma treatment using an ionized gas plasma, preferably selected from the group consisting of helium, argon, nitrogen, neon, silane, hydrogen, oxygen and mixtures thereof. Preferably, a plasma treatment using an ionized oxygen gas plasma was used.

The plasma treatment was conducted using a Plasma treatment machine from Diener (Diener electronics; Plasma-Surface-Technology; Ebhausen, Germany), within a vacuum chamber for a time of 5 to 20 minutes, preferably 8 to 15 minutes. The treatment parameters were set as follows: Pressure within the vacuum chamber: 0.40 mbar; power: 35 W; oxygen gas flow: 5 sccm (min)-60 sccm (max).

The plasma treatment was found to significantly increase the hydrophilic properties of the PLLA top layer—independent of the presence of a collagen coating—but not of the PLGA layer. The latter stayed hydrophobic.

Sterilization

Either with collagen coating on the top layer or without, the matrices were subsequently sterilized by placing them in a H$_2$O$_2$-containing environment at a temperature below 40° C. The H$_2$O$_2$-containing environment was created within a vacuum chamber, by placing the matrix into the chamber, together with an open flask or dish containing a H$_2$O$_2$ solution and by subsequently evacuating the chamber to evaporate the H$_2$O$_2$. The H$_2$O$_2$ solution comprises H$_2$O$_2$ in an amount of 30% by volume or less. The treatment time depends highly on the pressure within the chamber and the concentration of the H$_2$O$_2$ solution. The pressure within the chamber is such that evaporation of the hydrogen peroxide occurs. Preferred (negative) pressures are in the range of $10^{-2}$ to $10^{-6}$ bar, preferably within the range of 0.1 to 20.0 mbar, e.g. 9 mbar. Preferred treatment times are at least two minutes, e.g. 2 to 30 minutes. However, in particular at pressures above 1 mbar, e.g. about 10 mbar, and/or lower temperatures (e.g. below 35° C.) and/or low hydrogen peroxide concentration (e.g. below 30 vol.-%), treatment times were preferably longer than one hour, e.g. 8 to 10 hours.

Static Contact Angle Measurements, Sessile Drop Method

Contact angle measurements were performed in order to determine the degree of hydrophilicity or hydrophobicity. Usually, the contact angles of the top and bottom layers of the matrix were determined by static contact angle measurements, using a sessile drop test with ultrapure water (Easy-Drop DSA20E, Krüss GmbH). The droplet size for the contact angle measurements was set to 0.1 µl. Contact angles were calculated by fitting a circular segment function to the contour of the droplet placed on the surface (circle fitting procedure).

The invention claimed is:

1. A biodegradable matrix for preventing post-surgical adhesions, surgery, within the body of a mammal, the matrix comprising
    a top layer made of a first biocompatible polymer material comprising poly(lactic acid) as a main component and optionally at least one further polymer selected from the group consisting of poly(glycolic acid), poly(glycolic acid-lactic acid) and mixtures thereof; and
    a bottom layer made of a second biocompatible polymer material comprising as a main component at least one polymer selected from the group consisting of poly(glycolic acid), poly(lactic acid), poly(glycolic acid-lactic acid) and mixtures thereof;
    wherein the content of poly(lactic acid) in the first polymer material is higher than in the second polymer material;
    wherein the two layers are formed as porous scaffolds comprising a sponge-like structure with interconnected pores of different sizes,
    the top layer being hydrophilic, having a water contact angle of less than 75° and
    the bottom layer being hydrophobic, having a water contact angle of more than 90°.

2. The matrix of claim 1, wherein the top layer has a water contact angle of less than 60°.

3. The matrix of claim 1, wherein the two layers are either integrally formed or firmly connected with one another along a common interface.

4. The matrix of claim 1, wherein the two layers are provided as two individual structures that are separate from one another.

5. The matrix of claim 1, wherein the first polymer material consists of at least 70% poly(lactic acid).

6. The biodegradable matrix of claim 1, wherein at least one of the two layers has a flat sheet-like shape and is elastically deformable to allow folding or rolling thereof.

7. The matrix claim 1, having a total degradation time in the mammal of less than 24 months, with the top layer having a degradation time of less than 6 months and the bottom layer having a degradation time of more than 4 months.

8. The matrix of claim 1, wherein one of the two layers has a faster degradation rate than the other layer.

9. The matrix of claim 1, wherein the top layer comprises or is covered with at least one natural polymer selected from the group consisting of collagen, gelatin, laminin, fibrinogen, albumin, chitin, chitosan, agarose, hyaluronic acidalginate and mixtures thereof.

10. A method for preparing the biodegradable matrix of claim 1, the method comprising:
    a) preparing a first mixture I of salt particulates and a dissolved first polymer material comprising poly(lactic acid) as a main component and optionally at least one further polymer selected from the group consisting of poly(glycolic acid), poly(glycolic acid-lactic acid) and mixtures thereof;
    b) spreading the first mixture I on a surface to form a first layer;
    c) preparing a second mixture II of salt particulates and a dissolved second polymer material comprising at least one polymer selected from the group consisting of poly(glycolic acid), poly(lactic acid), poly(glycolic acid-lactic acid) and mixtures thereof, wherein the content of poly(lactic acid) in the first polymer material is higher than in the second polymer material;
    d) depositing a layer of the second mixture II of step c) on top of the first layer of step b);
    e) drying the resulting structure to obtain a two-layered biodegradable matrix with a bottom layer of second polymer material and a top layer of first polymer material; and
    plasma treating the matrix with an oxidized gas plasma at a temperature below 50° C.

11. The method of claim 10, wherein the first polymer material consists of at least 70% of poly(lactic acid).

12. The method of claim 10, wherein the plasma treatment is conducted for 2 to 30 minutes, and at a pressure within the range of $10^{-2}$ to $10^{-6}$ bar.

13. The method of claim 10, further comprising a step of covering the top layer of the matrix obtained in step d) with a natural polymer selected from the group consisting of collagen, gelatin, laminin, fibrinogen, albumin, chitin, chitosan, agarose, hyaluronic acidalginate and mixtures thereof.

14. The method of claim 10, further comprising a step g) of sterilizing the resulting matrix by treating it with hydrogen peroxide at a temperature below 50° C.

15. The method of claim 14, wherein the hydrogen peroxide treatment in step g) is conducted by exposing the matrix to a $H_2O_2$ plasma or a $H_2O_2$ containing atmosphere, under reduced pressure, in the range of $10^{-2}$ to $10^{-6}$ bar, and for at least 2 minutes.

16. The matrix of claim 1, wherein the top layer has a water contact angle of less than 45°.

17. The matrix of claim 1, wherein the top layer has a water contact angle of less than 25°.

18. The matrix of claim 1, wherein the top layer has a water contact angle of less than 15°.

19. The matrix of claim 1, wherein the top layer has a water contact angle within the range of 0° to 10°.

20. The matrix of claim 1, wherein the first polymer material consists of at least 80% poly(lactic acid).

21. The matrix of claim 1, wherein the first polymer material consists essentially of poly(lactic acid).

22. The matrix of claim 1, wherein each of the two layers has a flat sheet-like shape and is elastically deformable to allow folding or rolling thereof.

23. The matrix of claim 1, wherein the top layer has a degradation time of less than 4 months, and the bottom layer has a degradation time of between 4 and 12 months.

24. The matrix of claim 8, wherein the top layer has a faster degradation rate than the other layer.

25. The matrix of claim 9, wherein the at least one natural polymer is collagen.

26. The method of claim 10, wherein the plasma treatment is conducted for 5 to 20 minutes at a pressure within the range of 0.1 to 1.0 mbar.

27. The method of claim 13, wherein the natural polymer is collagen.

28. The method of claim 14, wherein the hydrogen peroxide treatment in step g) is conducted by exposing the matrix to a $H_2O_2$ plasma or a $H_2O_2$ containing atmosphere, under reduced pressure, within the range of 0.1 to 20.0 mbar, and for at least 2 minutes.

29. The method of claim 14, wherein the hydrogen peroxide treatment in step g) is conducted by exposing the matrix to a $H_2O_2$ plasma or a $H_2O_2$ containing atmosphere, under reduced pressure, within the range of 0.1 to 20.0 mbar, and for at least 2 to 30 minutes.

30. The method of claim 14, wherein the hydrogen peroxide treatment in step g) is conducted by exposing the matrix to a $H_2O_2$ plasma or a $H_2O_2$ containing atmosphere, under reduced pressure in the range of 0.1 to 20.0 mbar, and for several hours.

31. The matrix of claim 1, wherein the post-surgical adhesions are prevented after soft tissue repair following abdominal surgery.

\* \* \* \* \*

UNITED STATES PATENT AND TRADEMARK OFFICE
CERTIFICATE OF CORRECTION

PATENT NO. : 12,059,510 B2
APPLICATION NO. : 17/435501
DATED : August 13, 2024
INVENTOR(S) : Hans Ulrich Baer Page 1 of 1

It is certified that error appears in the above-identified patent and that said Letters Patent is hereby corrected as shown below:

In the Claims

Column 17, Line 9, Claim 1, delete "adhesions, surgery," and insert -- adhesions --

Column 17, Line 10, Claim 1, delete "comprising" and insert -- comprising: --

Column 17, Line 44, Claim 7, delete "matrix" and insert -- matrix of --

Signed and Sealed this
Twenty-second Day of October, 2024

Katherine Kelly Vidal
*Director of the United States Patent and Trademark Office*